(12) United States Patent
Reiley

(10) Patent No.: US 8,840,651 B2
(45) Date of Patent: Sep. 23, 2014

(54) SYSTEMS AND METHODS FOR THE FIXATION OR FUSION OF BONE

(71) Applicant: SI-Bone, Inc., San Jose, CA (US)

(72) Inventor: Mark A. Reiley, Washington, DC (US)

(73) Assignee: SI-Bone Inc., San Jose, CA (US)

( * ) Notice: Subject to any disclaimer, the term of this patent is extended or adjusted under 35 U.S.C. 154(b) by 0 days.

(21) Appl. No.: 13/674,764

(22) Filed: Nov. 12, 2012

(65) Prior Publication Data

US 2013/0131739 A1  May 23, 2013

Related U.S. Application Data

(60) Continuation of application No. 12/072,153, filed on Feb. 25, 2008, now Pat. No. 8,308,779, which is a division of application No. 10/914,629, filed on Aug. 9, 2004, now abandoned.

(51) Int. Cl.
| | |
|---|---|
| *A61B 17/84* | (2006.01) |
| *A61B 17/86* | (2006.01) |
| *A61B 17/68* | (2006.01) |
| *A61F 2/44* | (2006.01) |
| *A61F 2/30* | (2006.01) |
| *A61F 2/28* | (2006.01) |
| *A61F 2/42* | (2006.01) |
| *A61F 2/00* | (2006.01) |
| *A61B 17/16* | (2006.01) |

(52) U.S. Cl.
CPC ........ *A61B 17/846* (2013.01); *A61F 2220/0025* (2013.01); *A61F 2310/00329* (2013.01); *A61F 2002/448* (2013.01); *A61F 2002/30405* (2013.01); *A61F 2002/30576* (2013.01); *A61F 2230/0023* (2013.01); *A61B 17/8685* (2013.01); *A61F 2002/30179* (2013.01); *A61B 17/866* (2013.01); *A61F 2002/30841* (2013.01); *A61B 17/68* (2013.01); *A61F 2310/00023* (2013.01); *A61F 2310/0097* (2013.01); *A61F 2/4465* (2013.01); *A61F 2310/00131* (2013.01); *A61F 2310/00796* (2013.01); *A61F 2002/30235* (2013.01); *A61F 2/28* (2013.01); *A61F 2310/00017* (2013.01); *A61F 2002/30156* (2013.01); *A61F 2310/00179* (2013.01); *A61F 2002/3082* (2013.01); *A61F 2002/3023* (2013.01); *A61F 2002/4238* (2013.01); *A61F 2310/00029* (2013.01); *A61F 2002/3085* (2013.01); *A61F 2/447* (2013.01); *A61F 2/30767* (2013.01); *A61F 2002/30604* (2013.01); *A61F 2002/30622* (2013.01); *A61B 17/864* (2013.01); *A61F 2002/30787* (2013.01); *A61F 2210/0004* (2013.01); *A61F 2002/30062* (2013.01); *A61F 2/0077* (2013.01); *A61F 2002/30777* (2013.10); *A61F 2230/0069* (2013.01); *A61F 2230/0058* (2013.01); *A61B 17/1615* (2013.01); *A61F 2002/305* (2013.01); *A61F 2/4455* (2013.01); *A61F 2002/30785* (2013.01)

USPC .......................................... 606/300; 606/301

(58) Field of Classification Search
USPC .................... 606/300–331; 623/17.11–17.16
See application file for complete search history.

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| EP | 1287796 A1 | 3/2003 |
| JP | 05-176942 A | 7/1993 |

(Continued)

OTHER PUBLICATIONS

Reiley, Mark A.; U.S. Appl. No. 12/357,483 entitled "Systems and methods for the fixation or fusion of bone in the hand and wrist," filed Jan. 22, 2009 (abandoned).

(Continued)

*Primary Examiner* — Nicholas Woodall
(74) *Attorney, Agent, or Firm* — Shay Glenn LLP

(57) ABSTRACT

A stem-like bone fixation device allows for bony in-growth on its surface and across fracture fragments or between bones that are to be fused.

16 Claims, 5 Drawing Sheets

(56) References Cited

U.S. PATENT DOCUMENTS

| | | | |
|---|---|---|---|
| 2,243,717 A | 5/1941 | Moreira | |
| 2,414,882 A | 7/1947 | Longfellow | |
| 2,675,801 A | 4/1954 | Bambara et al. | |
| 3,076,453 A | 2/1963 | Tronzo | |
| 3,506,982 A | 4/1970 | Steffee | |
| 3,694,821 A | 10/1972 | Moritz | |
| 3,709,218 A * | 1/1973 | Halloran | 606/64 |
| 4,341,206 A | 7/1982 | Perrett et al. | |
| 4,344,190 A | 8/1982 | Lee et al. | |
| 4,399,813 A | 8/1983 | Barber | |
| 4,475,545 A | 10/1984 | Ender | |
| 4,501,269 A | 2/1985 | Bagby | |
| 4,569,338 A | 2/1986 | Edwards | |
| 4,612,918 A | 9/1986 | Slocum | |
| 4,622,959 A | 11/1986 | Marcus | |
| 4,630,601 A | 12/1986 | Harder et al. | |
| 4,657,550 A | 4/1987 | Daher | |
| 4,743,256 A | 5/1988 | Brantigan | |
| 4,773,402 A | 9/1988 | Asher et al. | |
| 4,787,378 A | 11/1988 | Sodhi | |
| 4,790,303 A | 12/1988 | Steffee | |
| 4,834,757 A | 5/1989 | Brantigan | |
| 4,846,162 A * | 7/1989 | Moehring | 606/67 |
| 4,877,019 A * | 10/1989 | Vives | 606/64 |
| 4,878,915 A | 11/1989 | Brantigan | |
| 4,904,261 A | 2/1990 | Dove et al. | |
| 4,950,270 A | 8/1990 | Bowman et al. | |
| 4,961,740 A | 10/1990 | Ray et al. | |
| 5,034,011 A | 7/1991 | Howland | |
| 5,035,697 A | 7/1991 | Frigg | |
| 5,053,035 A | 10/1991 | McClaren | |
| 5,066,296 A * | 11/1991 | Chapman et al. | 606/64 |
| 5,102,414 A | 4/1992 | Kirsch | |
| 5,108,397 A | 4/1992 | White | |
| 5,122,141 A | 6/1992 | Simpson et al. | |
| 5,139,498 A | 8/1992 | Astudillo Ley | |
| 5,147,367 A | 9/1992 | Ellis | |
| 5,147,402 A | 9/1992 | Bohler et al. | |
| 5,190,551 A | 3/1993 | Chin et al. | |
| 5,197,961 A | 3/1993 | Castle | |
| 5,242,444 A | 9/1993 | MacMillan | |
| 5,298,254 A | 3/1994 | Prewett et al. | |
| 5,334,205 A | 8/1994 | Cain | |
| 5,443,466 A | 8/1995 | Shah | |
| 5,470,334 A | 11/1995 | Ross et al. | |
| 5,480,402 A | 1/1996 | Kim | |
| 5,489,284 A * | 2/1996 | James et al. | 606/62 |
| 5,569,249 A | 10/1996 | James et al. | |
| 5,593,409 A | 1/1997 | Michelson | |
| 5,609,636 A | 3/1997 | Kohrs et al. | |
| 5,626,616 A | 5/1997 | Speece | |
| 5,645,599 A | 7/1997 | Samani | |
| 5,658,337 A | 8/1997 | Kohrs et al. | |
| 5,667,510 A | 9/1997 | Combs | |
| 5,669,909 A | 9/1997 | Zdeblick et al. | |
| 5,672,178 A | 9/1997 | Petersen | |
| 5,683,391 A | 11/1997 | Boyd | |
| 5,713,904 A | 2/1998 | Errico et al. | |
| 5,716,358 A | 2/1998 | Ochoa et al. | |
| 5,743,912 A | 4/1998 | Lahille et al. | |
| 5,766,174 A | 6/1998 | Perry | |
| 5,788,699 A | 8/1998 | Bobst et al. | |
| 5,800,440 A | 9/1998 | Stead | |
| 5,868,749 A | 2/1999 | Reed | |
| 5,928,239 A | 7/1999 | Mirza | |
| 6,010,507 A | 1/2000 | Rudloff | |
| 6,053,916 A | 4/2000 | Moore | |
| 6,056,749 A | 5/2000 | Kuslich | |
| 6,096,080 A | 8/2000 | Nicholson et al. | |
| 6,120,504 A | 9/2000 | Brumback et al. | |
| 6,143,031 A | 11/2000 | Knothe et al. | |
| 6,210,442 B1 | 4/2001 | Wing et al. | |
| 6,214,049 B1 | 4/2001 | Gayer et al. | |
| 6,221,074 B1 | 4/2001 | Cole et al. | |
| 6,224,607 B1 | 5/2001 | Michelson | |
| 6,241,732 B1 | 6/2001 | Overaker et al. | |
| 6,270,528 B1 | 8/2001 | McKay | |
| 6,302,885 B1 | 10/2001 | Essiger | |
| 6,302,914 B1 | 10/2001 | Michelson | |
| 6,306,140 B1 * | 10/2001 | Siddiqui | 606/315 |
| 6,319,253 B1 | 11/2001 | Ackeret et al. | |
| 6,409,768 B1 * | 6/2002 | Tepic et al. | 623/23.27 |
| 6,451,020 B1 | 9/2002 | Zucherman et al. | |
| 6,471,707 B1 | 10/2002 | Miller et al. | |
| 6,485,518 B1 | 11/2002 | Cornwall et al. | |
| 6,497,707 B1 | 12/2002 | Bowman et al. | |
| 6,517,541 B1 | 2/2003 | Sesic | |
| 6,520,969 B2 | 2/2003 | Lambrecht et al. | |
| 6,524,314 B1 * | 2/2003 | Dean et al. | 606/64 |
| 6,527,775 B1 | 3/2003 | Warburton | |
| 6,565,566 B1 | 5/2003 | Wagner et al. | |
| 6,575,899 B1 | 6/2003 | Foley et al. | |
| 6,575,991 B1 | 6/2003 | Chesbrough et al. | |
| 6,579,293 B1 * | 6/2003 | Chandran | 606/64 |
| 6,582,431 B1 | 6/2003 | Ray | |
| 6,595,998 B2 | 7/2003 | Johnson et al. | |
| 6,602,293 B1 | 8/2003 | Biermann et al. | |
| 6,605,090 B1 | 8/2003 | Trieu et al. | |
| 6,607,530 B1 | 8/2003 | Carl et al. | |
| 6,635,059 B2 | 10/2003 | Randall et al. | |
| 6,666,868 B2 | 12/2003 | Fallin | |
| 6,669,529 B1 | 12/2003 | Scaries | |
| 6,673,075 B2 | 1/2004 | Santilli | |
| 6,692,501 B2 | 2/2004 | Michelson | |
| 6,723,099 B1 | 4/2004 | Goshert | |
| 6,740,118 B2 | 5/2004 | Eisermann et al. | |
| 6,743,257 B2 | 6/2004 | Castro | |
| 6,793,656 B1 | 9/2004 | Mathews | |
| 6,984,235 B2 | 1/2006 | Huebner | |
| 7,118,579 B2 | 10/2006 | Michelson | |
| 7,175,663 B1 | 2/2007 | Stone | |
| 7,211,085 B2 | 5/2007 | Michelson | |
| 7,223,269 B2 | 5/2007 | Chappuis | |
| 7,335,205 B2 | 2/2008 | Aeschlimann et al. | |
| 7,452,359 B1 | 11/2008 | Michelson | |
| 7,481,831 B2 | 1/2009 | Bonutti | |
| 7,534,254 B1 | 5/2009 | Michelson | |
| 7,569,054 B2 | 8/2009 | Michelson | |
| 7,648,509 B2 | 1/2010 | Stark | |
| 7,686,805 B2 | 3/2010 | Michelson | |
| 7,699,852 B2 | 4/2010 | Frankel et al. | |
| 7,758,646 B2 | 7/2010 | Khandkar et al. | |
| 7,887,565 B2 | 2/2011 | Michelson | |
| 7,909,832 B2 | 3/2011 | Michelson | |
| 7,922,765 B2 | 4/2011 | Reiley | |
| 7,942,879 B2 | 5/2011 | Christie et al. | |
| 8,066,705 B2 | 11/2011 | Michelson | |
| 8,066,709 B2 | 11/2011 | Michelson | |
| 8,202,305 B2 | 6/2012 | Reiley | |
| 8,308,779 B2 | 11/2012 | Reiley | |
| 8,388,667 B2 | 3/2013 | Reiley et al. | |
| 8,414,648 B2 | 4/2013 | Reiley | |
| 8,672,986 B2 | 3/2014 | Klaue et al. | |
| 2001/0046518 A1 | 11/2001 | Sawhney | |
| 2001/0047207 A1 | 11/2001 | Michelson | |
| 2001/0049529 A1 | 12/2001 | Cachia et al. | |
| 2002/0038123 A1 * | 3/2002 | Visotsky et al. | 606/73 |
| 2002/0049497 A1 | 4/2002 | Mason | |
| 2002/0120275 A1 | 8/2002 | Schmieding et al. | |
| 2002/0128652 A1 | 9/2002 | Ferree | |
| 2002/0143335 A1 | 10/2002 | von Hoffmann et al. | |
| 2002/0151903 A1 | 10/2002 | Takei et al. | |
| 2002/0183858 A1 | 12/2002 | Contiliano et al. | |
| 2002/0198527 A1 | 12/2002 | Mückter | |
| 2003/0018336 A1 | 1/2003 | Vandewalle | |
| 2003/0032961 A1 | 2/2003 | Pelo et al. | |
| 2003/0065332 A1 | 4/2003 | TenHuisen et al. | |
| 2003/0074000 A1 | 4/2003 | Roth et al. | |
| 2003/0083688 A1 | 5/2003 | Simonson | |
| 2003/0097131 A1 | 5/2003 | Schon et al. | |
| 2003/0199983 A1 | 10/2003 | Michelson | |
| 2003/0233147 A1 | 12/2003 | Nicholson et al. | |
| 2004/0024458 A1 | 2/2004 | Senegas et al. | |
| 2004/0073216 A1 | 4/2004 | Lieberman | |

(56) References Cited

U.S. PATENT DOCUMENTS

| | | |
|---|---|---|
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0147929 A1 | 7/2004 | Biedermann et al. |
| 2004/0181282 A1 | 9/2004 | Zucherman et al. |
| 2004/0225360 A1 | 11/2004 | Malone |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0107878 A1 | 5/2005 | Conchy |
| 2005/0124993 A1 | 6/2005 | Chappuis |
| 2005/0137605 A1 | 6/2005 | Assell et al. |
| 2005/0159749 A1 | 7/2005 | Levy et al. |
| 2005/0165398 A1 | 7/2005 | Reiley |
| 2005/0228384 A1 | 10/2005 | Zucherman et al. |
| 2005/0246021 A1 | 11/2005 | Ringeisen et al. |
| 2006/0036247 A1 | 2/2006 | Michelson |
| 2006/0036251 A1 | 2/2006 | Reiley |
| 2006/0058793 A1 | 3/2006 | Michelson |
| 2006/0129247 A1 | 6/2006 | Brown et al. |
| 2006/0161163 A1 | 7/2006 | Shino |
| 2007/0083265 A1 | 4/2007 | Malone |
| 2007/0149976 A1 | 6/2007 | Hale et al. |
| 2007/0156241 A1 | 7/2007 | Reiley et al. |
| 2007/0156246 A1 | 7/2007 | Meswania et al. |
| 2008/0065215 A1 | 3/2008 | Reiley |
| 2008/0109083 A1 | 5/2008 | Van Hoeck et al. |
| 2009/0043393 A1 | 2/2009 | Duggal et al. |
| 2009/0259261 A1 | 10/2009 | Reiley |
| 2010/0145461 A1 | 6/2010 | Landry et al. |
| 2010/0191292 A1 | 7/2010 | DeMeo et al. |
| 2011/0087294 A1 | 4/2011 | Reiley |
| 2011/0118785 A1 | 5/2011 | Reiley |
| 2011/0118790 A1 | 5/2011 | Reiley |
| 2011/0118796 A1 | 5/2011 | Reiley et al. |
| 2011/0125268 A1 | 5/2011 | Reiley |
| 2011/0184478 A1 | 7/2011 | Reiley |
| 2013/0184769 A1 | 7/2013 | Reiley et al. |
| 2013/0226301 A1 | 8/2013 | Reiley |

FOREIGN PATENT DOCUMENTS

| | | |
|---|---|---|
| JP | 2004512895 | 4/2004 |
| JP | 2004516866 | 6/2004 |
| WO | WO02/38054 | 5/2002 |
| WO | WO03/007839 A2 | 1/2003 |
| WO | WO2004/002344 | 1/2004 |
| WO | WO2006003316 | 1/2006 |

OTHER PUBLICATIONS

Mauldin et al.; U.S. Appl. No. 13/791,746 entitled "Integrated implant," filed Mar. 8, 2013.

Mauldin, R. G.; U.S. Appl. No. 13/791,801 entitled "Threaded implant," filed Mar. 8, 2013.

Mauldin, R. G.; U.S. Appl. No. 13/791,837 entitled "Artificial joint," filed Mar. 8, 2013.

Mauldin, R. G.; U.S. Appl. No. 13/791,849 entitled "Revision tool and method," filed Mar. 8, 2013.

Mauldin et al.; U.S. Appl. No. 13/794,542 entitled "Tissue dilator and protector," filed Mar. 11, 2013.

Mauldin et al.; U.S. Appl. No. 13/794,580 entitled "Guide pin," filed Mar. 11, 2013.

Mauldin et al.; U.S. Appl. No. 13/794,611 entitled "Impactor," filed Mar. 11, 2013.

Reiley, Mark; U.S. Appl. No. 13/867,941 entitled "Apparatus, systems, and methods for achieving anterior lumbar interbody fusion," filed Apr. 22, 2013.

Mauldin et al.; U.S. Appl. No. 13/888,249 entitled "Fenestrated Implant," filed May 6, 2013.

Reiley, Mark; U.S. Appl. No. 13/898,415 entitled "Apparatus, systems, and methods for achieving lumbar facet fusion," filed May 20, 2013.

Reiley, Mark; U.S. Appl. No. 13/925,678 entitled "Apparatus, systems, and methods for stabilizing a spondylolisthesis" filed Jun. 24, 2013.

Reiley, Mark A.; U.S. Appl. No. 14/162,689 entitled "Systems and methods for the fixation or fusion of bone,", filed Jan. 23, 2014.

\* cited by examiner

SYSTEMS AND METHODS FOR THE FIXATION OR FUSION OF BONE

CROSS REFERENCE TO RELATED APPLICATIONS

This application is a continuation of U.S. patent application Ser. No. 12/072,153, filed on Feb. 25, 2008, entitled "Systems and Methods for the Fixation or Fusion of Bone," now U.S. Pat. No. 8,308,779; which is a divisional of U.S. patent application Ser. No. 10/914,629, filed Aug. 9, 2004, and entitled "Systems and Methods for the Fixation or Fusion of Bone," now U.S. Patent Application Publication No. 2006-0036251-A1, now abandoned, which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to the fixation of bone.

BACKGROUND

Many types of hardware are available both for fracture fixation and for the fixation of bones that are to fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE DISCLOSURE

The invention provides bone fixation devices and related methods for stabilizing bone segments. The systems and methods include a stem-like structure adapted for passage between adjacent bone segments. At least a portion of the stem-like structure includes a surface that enhances bony in-growth. Boney in-growth into the stem-like structure helps speed up the fusion process or fracture healing time.

In some embodiments, a method for the fixation or fusion of a first bone segment to a second bone segment across a joint is provided. The method includes providing an elongate implant having a proximal end, a distal end, a longitudinal axis, and a lumen extending through the elongate implant along the longitudinal axis, wherein the elongate implant has a tapered distal end and a first fenestration positioned on a middle portion of elongate implant such that the first fenestration is offset from both the distal end and the proximal end; and inserting the elongate implant through the first bone segment and across the joint and into the second bone segment such that the first fenestration lies at least partly in the joint between the first bone segment and the second bone segment.

In some embodiments, the first fenestration is oblong and oriented parallel to the longitudinal axis. In some embodiments, the elongate implant further comprises a second fenestration sized and shaped like the first fenestration and positioned opposite the first fenestration such that an opening is formed completely through the elongate implant.

In some embodiments, the elongate implant comprises external screw threads. In some embodiments, the external screw threads are located on a distal portion of the elongate implant. In some embodiments, the step of inserting the elongate implant comprises screwing the elongate implant through the first bone segment and across the joint and into the second bone segment.

In some embodiments, the elongate implant is coated with a material that promotes bony in-growth. In some embodiments, the material is hydroxyapatite.

In some embodiments, the method further includes inserting a guide pin through the first bone segment and across the joint and into the second bone segment, wherein the step of inserting the elongate implant comprises inserting the elongate implant over the guide pin. In some embodiments, the method further includes inserting a cannulated drill bit over the guide pin and drilling a bore through the first bone segment and across the joint and into the second bone segment. In some embodiments, the bore is the same cross-sectional dimension as the implant. In some embodiments, the bore has a smaller cross-sectional dimension than the implant.

In some embodiments, the method further includes providing a second elongate implant having a proximal end, a distal end, a longitudinal axis, and a lumen extending through the second elongate implant along the longitudinal axis of the second elongate implant, wherein the second elongate implant has a tapered distal end; and inserting the second elongate implant through the first bone segment and across the joint and into the second bone segment.

In some embodiments, the second elongate implant has a fenestration positioned on a middle portion of second elongate implant such that the fenestration of the second elongate implant is offset from both the distal end and the proximal end of the second elongate implant. In some embodiments, the second elongate implant is inserted such that the fenestration of the second elongate implant lies at least partly in the joint between the first bone segment and the second bone segment. In some embodiments, the elongate implant and the second elongate implant have the same size. In some embodiments, the elongate implant and the second elongate implant are of different size.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1:
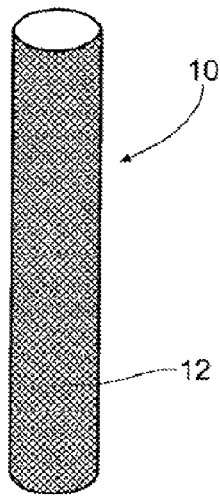
FIG. 1 is a perspective view of a bone fixation stem having a boney in-growth surface of a mesh configuration.

FIG. 1 shows a device 10 sized and configured for the fixation of bone fractures or for the fixation of bones which are to be fused (arthrodesed). The device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The device 10 can take various shapes and have various cross-sectional geometries. The device 10 can have, e.g., a generally curvilinear (i.e., round or oval) cross-section, or a generally rectilinear cross section (i.e., square or rectangular), or combinations thereof. As will be described in greater detail later, the device 10 can be conical or wedge shaped.

The structure 10 includes surface texturing 12 along at least a portion of its length to promote bony in-growth on its surface. The surface texturing 12 can comprise, e.g., through holes, and/or various surface patterns, and/or various surface textures, and/or pores, or combinations thereof. The device 10 can be coated or wrapped or surfaced treated to provide the surface texturing 12, or it can be formed from a material that itself inherently possesses a surface conducing to bony in-growth, such as a porous mesh, hydroxyapetite, or other porous surface. The device 10 may further be covered with various other coatings such as antimicrobial, antithrombotic, and osteoinductive agents, or a combination thereof. The surface texturing 12 may be impregnated with such agents, if desired.

Figure 2:
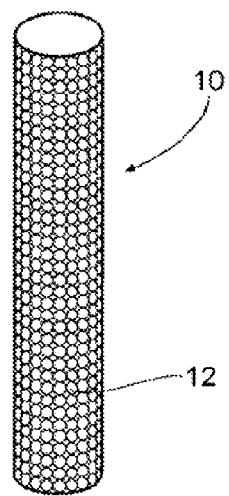
FIG. 2 is a perspective view of an alternative embodiment of a bone fixation stem having a boney in-growth surface of a beaded configuration.
Figure 3:
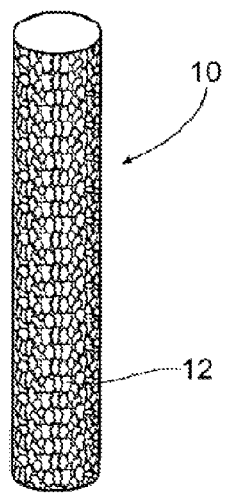
FIG. 3 is a perspective view of an alternative embodiment of a bone fixation stem having a boney in-growth surface of a trabecular configuration.

The configuration of the surface texturing 12 can, of course, vary. By way of examples, FIG. 1 shows the surface 12 as an open mesh configuration; FIG. 2 shows the surface 12 as beaded configuration; and FIG. 3 shows the surface 12 as a trabecular configuration. Any configuration conducive to bony in-growth will suffice.

Figure 4:
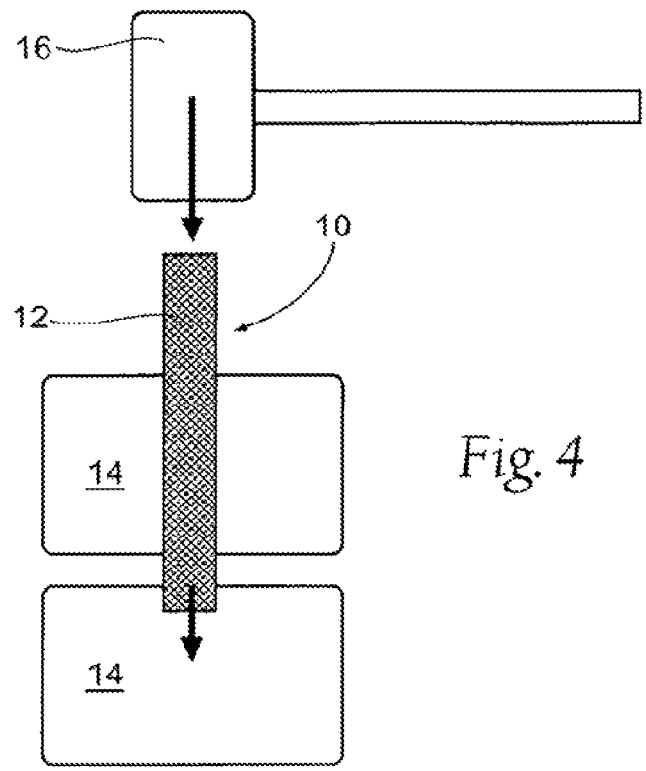
FIG. 4 is a schematic view of a bone fixation stem of the type shown in Fig. being inserted into bone across a fracture line or bone joint.

In use (see FIGS. 4 and 5), the device 10 is inserted into a space between two adjacent bone surfaces, e.g., into a fracture site or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth surface 12 along the surface of the device 10 accelerates bony in-growth into the device 10. Boney in-growth into the device 10 helps speed up the fusion process or fracture healing time.

Figure 5:
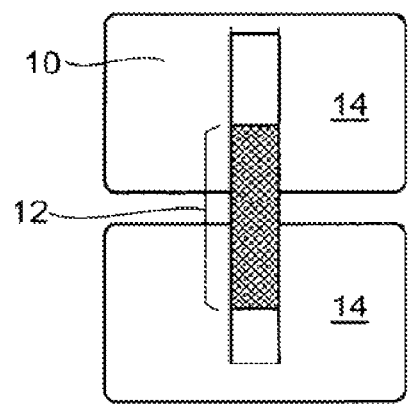
FIG. 5 is a schematic view of a bone fixation stem positioned within bone and illustrating a boney in-growth surface of the stem extending across a fracture line or bone joint.

The bony in-growth surface 12 may cover the entire outer surface of the device 10, as shown in FIG. 4, or the bony in-growth surface 12 may cover just a specified distance on either side of the joint surface or fracture line, as shown in FIG. 5.

The size and configuration of the device 10 can be varied to accommodate the type and location of the bone to be treated as well as individual anatomy.

Figure 6:
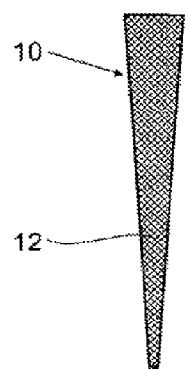
FIG. 6 is a front plan view of an alternative embodiment of a bone fixation stem having a boney in-growth surface in which the stem has a conical configuration.
Figure 7:
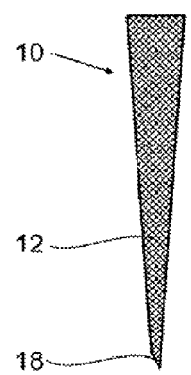
FIG. 7 is front plan view of an alternative embodiment of a bone fixation stem having a boney in-growth surface in which the stem has a beveled distal tip.
Figure 8A:
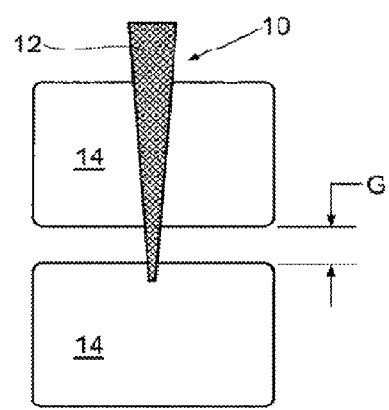
FIGS. 8A and 8B are schematics illustrating the insertion of a conical bone fixation stem of the type shown in FIG. 6 to reduce the gap between bone segments.
Figure 8B:
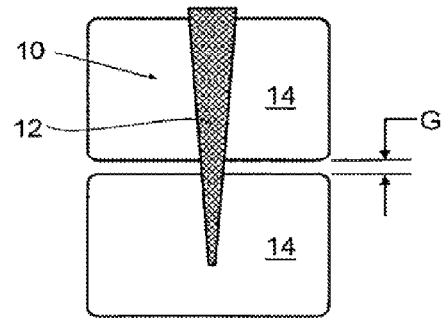

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the joint surfaces or fracture fragments together, reducing the gap (G) between the bone segments 14

Figure 9:
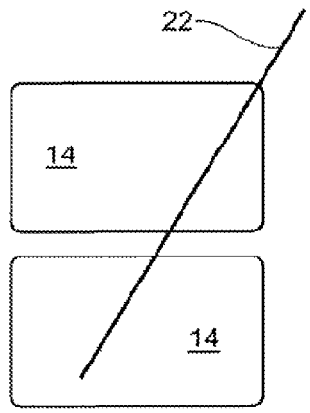
FIG. 9 is a schematic illustrating a guidewire being introduced into bone across bone segments.
Figure 10:
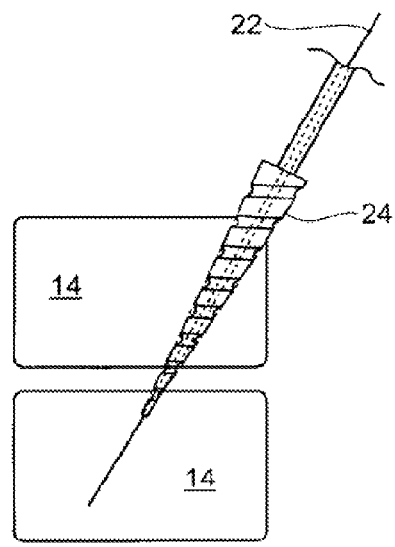
FIG. 10 is a schematic similar to FIG. 9 and illustrating a drill bit being introduced over the guidewire.
Figure 11:
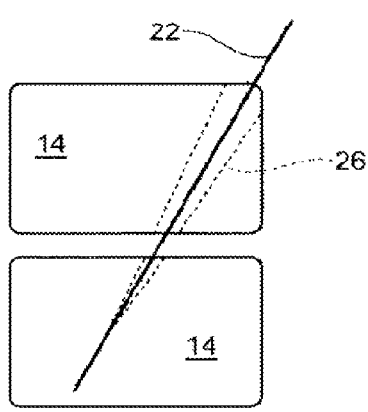
FIG. 11 is a schematic similar to FIG. 10 and illustrating a bore formed in the bone remaining after withdrawal of the drill bit.
Figure 12:
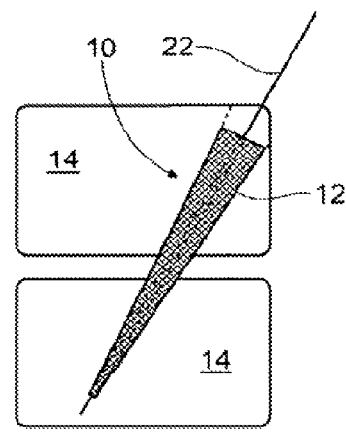
FIG. 12 is a schematic similar to FIG. 11 and illustrating insertion of a bone fixation stem into the pre-formed bore.

In FIGS. 9 to 12, the device 10 is cannulated, having a central lumen or throughbore 20 extending through it, to assist in the placement of the device 10 within bone In use, the physician can insert a conventional guide pin 22 through the bone segments 14 by conventional methods, as FIG. 9 shows. A cannulated drill bit 24 can then be introduced over the guide pin 22, as seen in FIG. 10. A single or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the device 10 itself can include screw-like threads along the body for screwing the device into place. In the arrangement, the device 10 can be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
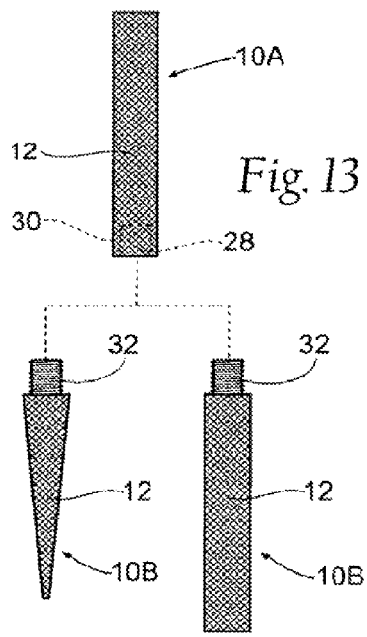
FIG. 13 is an exploded front plan view illustrating the coupling of a pair of bone fixation stems by threaded engagement.

In many cases, it may be desirable to couple a series of devices 10 together, e.g., to provide stabilization over a larger surface area. A series of devices 10 may be coupled together be any suitable means, e.g., by a snap fit engagement or a groove and tab key arrangement. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
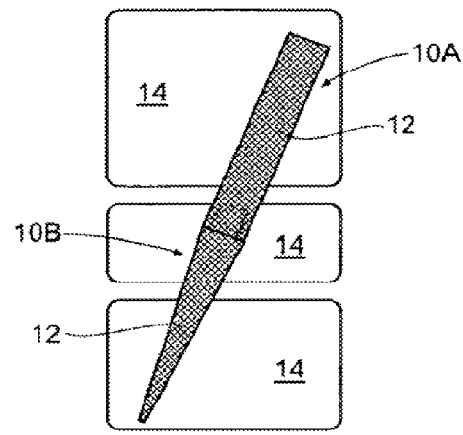
FIG. 14 is a schematic illustrating a pair of bone fixation stems coupled together and inserted into bone across multiple bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
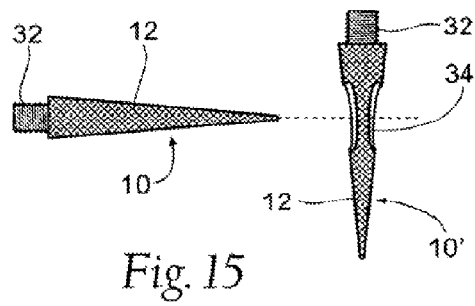
FIG. 15 is a front plan view illustrating passage of a bone fixation stem through a fenestration in another bone fixation stem.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the second device 10'.

Figure 16:
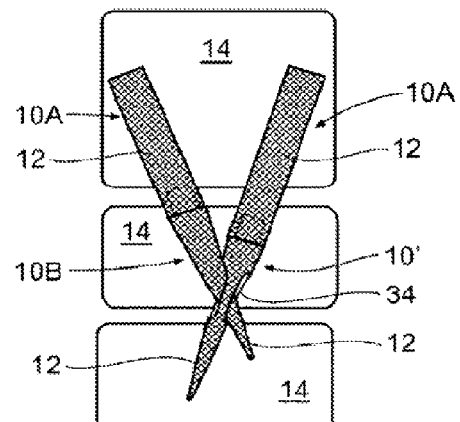
FIG. 16 is a schematic illustrating the placement of a series of bone fixation stems in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for the fixation or fusion of a first bone segment to a second bone segment across a joint, the method comprising:
providing an elongate implant having a proximal end, a distal end, a longitudinal axis, and a lumen extending through the elongate implant along the longitudinal axis, wherein the elongate implant has a tapered distal end and a first fenestration positioned on a middle portion of elongate implant such that the first fenestration is offset from both the distal end and the proximal end, wherein the elongate implant is made from a metal or metal alloy, wherein the elongate implant comprises external screw threads; and
inserting the elongate implant through the first bone segment and across the joint and into the second bone segment at a first location such that the first fenestration lies at least partly in the joint between the first bone segment and the second bone segment.

2. The method of claim 1, wherein the first fenestration is oblong and oriented parallel to the longitudinal axis.

3. The method of claim 1, wherein the elongate implant further comprises a second fenestration sized and shaped like the first fenestration and positioned opposite the first fenestration such that an opening is formed completely through the elongate implant.

4. The method of claim, wherein the external screw threads are located on a distal portion of the elongate implant.

5. The method of claim 1, wherein the step of inserting the elongate implant comprises screwing the elongate implant through the first bone segment and across the joint and into the second bone segment.

6. The method of claim 1, wherein the elongate implant is coated with a material that promotes bony in-growth.

7. The method of claim 6, wherein the material is hydroxyapatite.

8. A method for the fixation or fusion of a first bone segment to a second bone segment across a joint, the method comprising:
providing an elongate implant having a proximal end, a distal end, a longitudinal axis, and a lumen extending through the elongate implant along the longitudinal axis, wherein the elongate implant has a tapered distal end and a first fenestration positioned on a middle portion of elongate implant such that the first fenestration is offset from both the distal end and the proximal end, wherein the elongate implant is made from a metal or metal alloy;
inserting a guide pin through the first bone segment and across the joint and into the second bone segment; and
inserting the elongate implant over the guide pin and through the first bone segment and across the joint and into the second bone segment at a first location such that the first fenestration lies at least partly in the joint between the first bone segment and the second bone segment.

9. The method of claim 8, further comprising inserting a cannulated drill bit over the guide pin and drilling a bore through the first bone segment and across the joint and into the second bone segment.

10. The method of claim 9, wherein the bore is the same cross-sectional dimension as the implant.

11. The method of claim 9, wherein the bore has a smaller cross-sectional dimension than the implant.

12. A method for the fixation or fusion of a first bone segment to a second bone segment across a joint, the method comprising:
providing an elongate implant having a proximal end, a distal end, a longitudinal axis, and a lumen extending through the elongate implant along the longitudinal axis, wherein the elongate implant has a tapered distal end and a first fenestration positioned on a middle portion of elongate implant such that the first fenestration is offset from both the distal end and the proximal end, wherein the elongate implant is made from a metal or metal alloy;
providing a second elongate implant having a proximal end, a distal end, a longitudinal axis, and a lumen extending through the second elongate implant along the longitudinal axis of the second elongate implant, wherein the second elongate implant has a tapered distal end, wherein the second elongate implant has a fenestration positioned on a middle portion of second elongate implant such that the fenestration of the second elongate implant is offset from both the distal end and the proximal end of the second elongate implant;

inserting the elongate implant through the first bone segment and across the joint and into the second bone segment at a first location such that the first fenestration lies at least partly in the joint between the first bone segment and the second bone segment; and inserting the second elongate implant through the first bone segment and across the joint and into the second bone segment at a second location.

13. The method of claim 12, wherein the second elongate implant is inserted such that the fenestration of the second elongate implant lies at least partly in the joint between the first bone segment and the second bone segment.

14. The method of claim 12, wherein the elongate implant and the second elongate implant have the same size.

15. The method of claim 12, wherein the elongate implant and the second elongate implant are of different size.

16. The method of claim 12, wherein the size of the first elongate implant is determined in part by the first location and the size of the second elongate implant is determined in part by the second location.

* * * * *

UNITED STATES PATENT AND TRADEMARK OFFICE
CERTIFICATE OF CORRECTION

PATENT NO. : 8,840,651 B2  
APPLICATION NO. : 13/674764  
DATED : September 23, 2014  
INVENTOR(S) : Mark A. Reiley et al.

Page 1 of 1

It is certified that error appears in the above-identified patent and that said Letters Patent is hereby corrected as shown below:

Title Page, item (71); after "Applicant:" delete "SI-Bone, Inc., San Jose, CA (US)" and insert
--SI-Bone Inc., San Jose, CA (US)--.

In the Claims,

Claim 4, column 6, line 16; after "The method" and before "wherein the external", delete "of claim," and insert --of claim 1,--.

Signed and Sealed this  
Ninth Day of June, 2015

Michelle K. Lee  
*Director of the United States Patent and Trademark Office*